United States Patent
Comelli et al.

(10) Patent No.: US 6,864,285 B1
(45) Date of Patent: Mar. 8, 2005

(54) COVALENT DERIVATIVES OF ALKANOLAMIDES OF MONOCARBOXYLIC AND DICARBOXYLIC ACIDS FUNCTIONALLY ACTIVE ON THE CB2 CANNABINOID RECEPTOR

(75) Inventors: Cristina Comelli, Padua (IT); Francesco Della Valle, Padua (IT); Maria Federica Della Valle, Padua (IT); Gabriele Marcolongo, Due Carrare-Padova (IT)

(73) Assignee: Innovet Italia S.r.l., Milan (IT)

( * ) Notice: Subject to any disclaimer, the term of this patent is extended or adjusted under 35 U.S.C. 154(b) by 0 days.

(21) Appl. No.: 10/030,061

(22) PCT Filed: Jul. 7, 1999

(86) PCT No.: PCT/IT99/00207

§ 371 (c)(1),
(2), (4) Date: Jan. 4, 2002

(87) PCT Pub. No.: WO01/04083

PCT Pub. Date: Jan. 18, 2001

(51) Int. Cl.$^7$ .................. A61K 43/00; C07C 233/00
(52) U.S. Cl. .................. 514/478; 514/512; 514/546; 514/551; 514/625; 549/475; 554/52; 554/56; 554/63; 558/275; 558/276; 560/14; 560/33; 560/155; 560/165; 560/173

(58) Field of Search ............ 560/165, 14, 33, 560/155, 173; 514/478, 512, 546, 551, 625, 173; 549/475; 554/52, 56, 63; 558/275, 276

(56) References Cited

FOREIGN PATENT DOCUMENTS

| WO | WO 96/18391 | 6/1996 |
|---|---|---|
| WO | WO 96/18600 | 6/1996 |

*Primary Examiner*—Richard L. Raymond
(74) *Attorney, Agent, or Firm*—Kalow & Springut LLP

(57) ABSTRACT

The present invention relates to novel covalent derivatives of alkanolamides of monocarboxylic and dicarboxylic acids with aminoalcohols of general formula (I) which can usefully be used as agonists of the CB2 cannabinoid receptor and hence as drugs active in pathological conditions which can be controlled by stimulation and/or costimulation of this receptor

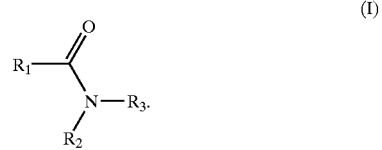

(I)

27 Claims, No Drawings

COVALENT DERIVATIVES OF ALKANOLAMIDES OF MONOCARBOXYLIC AND DICARBOXYLIC ACIDS FUNCTIONALLY ACTIVE ON THE CB2 CANNABINOID RECEPTOR

This application is a national stage application under 35 U.S.C. § 371 of International Application No. PCT/IT99/00207, filed Jul. 7, 1999, and published in English as WO 01/04083A1 on Jan. 18, 2001.

This application is a 35 U.S.C. § 371 application.

FIELD OF THE INVENTION

The present invention relates to novel covalent derivatives of alkanolamides of monocarboxylic and dicarboxylic acids with aminoalcohols which can usefully be used as agonists of the CB2 cannabinoid receptor and hence as drugs active in pathological conditions which can be controlled by stimulation and/or costimulation of this receptor.

PRIOR ART

Pharmacological effects of the cannabinoids not on the central nervous system, such as, for example, vascular and endo-ocular hypotensive effects and anti-asthmatic and muscle-relaxant effects have been known for some time but, because of the concomitant psychomimetic effects of these molecules, their therapeutic use is limited to the treatment of very serious pathological conditions such as the cachetic states associated with AIDS and, in any case, in particularly controlled clinical situations (Hollister L. E. Pharmacol. Rev. 1986, 38: 1–20). With regard to the multiplicity of the effects of the cannabinoids, the cell and molecular mechanisms upon which these are based are currently under active investigation.

Recent research has demonstrated the functions of the so-called CB cannabinoid receptors. Of these, the CB1 receptor, which was originally identified in the central nervous system (SNC), and the CB2 receptor, which is located mainly in peripheral cells of the immune system and has recently been found in the T-lymphocytes (Galiegue S. et al. Eur. J. Pharmacol. 1995, 232: 54–61; Munro S. et al. Nature 1993, 365: 61–65; Schatz A. R. et al. Tox. Appl. Pharmacol. 1997, 142: 248–287), have been studied in particular.

It is currently considered that the CB2 receptors can mediate the effects of the cannabinoids on cells of the immune system such as the mast cells and the lymphoctyes, by inhibitory modulation of the levels of pro-inflammatory cytokines which are expressed and secreted in excess by these cells when they are hyperactivated by exposure to tissue toxae of various kinds (Matsuda L. A. Cit. Rev. Neurobiol. 1997, 11: 143–146). It is therefore considered that functional agonists of the CB2 receptor—together with functional agonists of the CB1 receptor which have recently also been found at the level of the peripheral nervous system (Hohmann A. G. et al. 1997 Abstract Soc. Neurosci. 23: 1954; Richardson J. D. et al 1998 J. Neurosci. 18: 451–457) on cells of the immune system (Galiegue S. et al. Eur. J. Pharmacol. 1995, 232: 54–61) and on cells of the monocyte-macrophage line (Berdyshev E. V. et al. Eur. J. Pharmacol. 1997, 330: 231–240)—are essentially assigned the functions of controlling neuro-immuno-inflammatory processes (Richardson J. D. et al. Pain 1998, 75: 111–119; Calignano A. et al. Nature 1998, 394: 277–281). In these conditions, it has been shown that synergic functional activation of the CB2 receptor and of the CB1 receptor brings about maximum control of the neuro-immuno-inflammatory processes, including the hyperalgic phenomenon which frequently accompanies these processes (Calignano A. et al. Nature 1998, 394: 277–281). This synergy of action results from the simultaneous functional activation of the CB1 and CB2 receptors which are distributed and/or expressed differently, quantitatively, in tissue components functionally connected with one another in a mutual activator-effector relationship, on the basis of the chemical mediators released thereby under agonist stimulus (Calignano A. et al. Nature 1998, 394: 277–281; Levi-Montalcini R. et al. TINS 1996, 19: 514–520). It has been shown that the neurokine NGF is a fundamental modulator of the neuro-immuno-inflammatory processes triggered by noxae of various kinds, many of the cell populations being involved in these NGF-dependent processes for their survival, maturation, differentiation and gene expression (Levi-Montalcini R. et al. TINS 1996, 19: 514–520). It is in fact known that the receptor—known as trk—which has a high affinity for NGF, is expressed at the level of the peripheral nervous system, of the tissue macrophages, and of various cell lines with an immune character such as mast cells, basophilic cells and lymphoctyes. It is also known that these tissue populations also express the cannabinoid receptors CB1 and CB2, although with a different quantitative pattern (Galiegue S. et al. Eur. J. Pharmacol. 1995, 232: 54–61).

Recent results demonstrate a protective role of the CB2 receptor in neurodegenerative processes mediated by excitotoxic amino-acids (Skaper S. D. et al. Proc. Natl. Acad. Sci. U.S.A. 1996, 93: 3984–3989). It has very recently also been discovered that the viral protein gp120 of the HIV virus responsible for AIDS can stimulate, by interaction with a specific "supersite" which is present in a well-preserved region of the virus and which can thus act as a "superantigene" (Patella V. et al. J. Immunol. 1998, 161: 5647–5655), differential release from the mast cell of specific cytokines—in particular IL4 and IL13—which in turn are responsible for the maturation and the consequent prevalance of the Th2 cells of the immune system, by means of which the virus finds the best propagation conditions (Marone G.—Paper to the Congress of the Rome 5–7 March 199—Accademia Nazionale dei Lincei). It has also been shown that the Th2 cells of the immune system (with particular reference to the C4+ clone) express the trk receptor having a high affinity for NGF and themselves produce NGF as a result of antigenic stimulation (Ehrard P. B. et al. 1993 Proc. Acad. Sci. U.S.A. 90: 10984–10988).

NGF has recently been shown to facilitate and strengthen gene expression and replication of the HIV virus (Ensoli F. et al. 1994 (Virology, 200: 668–676). The levels of NGF neurokine in the serum of patients suffering from AIDS are particularly high and play a part in the progress of the disease (Pica F. et al. AIDS 1998, 12: 2025–2029). It has recently been shown that, in conditions of antigenic stimulation, high levels of NGF strengthen the return, proliferation and tissue differentiation of the circulating monocytes to macrophages. It is also known that macrophages, by means of suitable chemoreceptors, are tissue reservoirs of the virus and elements of increased tropism for the T-lymphocytes at the sites of inflammation where the propagation of HIV is greatly facilitated (Di Marzio P. et al. AIDS Res. H. Retrov. 1998, 14: 129–138; Gurwitz D. et al. Mol. Med. Today 1998, 4: 196–200). It has recently been shown that, as a result of antigenic stimulation, endocannabinoids functionally active at the CB1 and CB2 receptors modulate differentially the expression and/or the secretion of proinflammatory cytokine such as, of example, IL4, by the monocytes/macrophages (Berdishev E. V. et al. Eur. J. Pharmacol. 1997, 330: 231–240). It is also known that, not only the serum levels, but also the tissue levels of NGF are particularly high during neuro-immuno-inflammatory processes (Levi-Montalcini R. TINS 1996, 19: 514–520). The mast cell is the seat of synthesis, storage and release of biologically active NGF which is readily released by the mast cell in response to neurogenic and immunogenic stimuli (Leon A. et al. Proc. Natl. Acad. Sci. U.S.A., 91: 3739–3743). Both the antigenic stimulus represented by the viral protein gp120, and also the neurogenic stimulus represented by the substance P which is released at endothelial level in conditions of exposure to the HIV virus (Annunziata P. et al AIDS 1998, 12: 2377–2385) are activators of mast cell hyper-degranulation. In conditions of mast cell hyper-activation, the sensitization of NGF-mediated noxioceptive fibres with an increase in the levels of substance P released at the level of the peripheral nerve endings is known. It is known that this transmitter release may take place orthodromically by axonal reflex, or directly at peripheral level by means of an endogenic ligand not yet identified (Biro T. et al. J. Invest. Dermatol. 1997, 2: 56–60), owing to the activation of suitable vanilloid receptors—known as VRs—located both at the nerve endings and directly on the mast cell (Biro T. et al. Blood 1998, 91: 1332–1340).

In conditions of mast cell hyperactivation by neurogenic and immunogenic stimulus it is also known that the functional activation of the CB2 receptor expressed by the mast cell brings about an inhibitory modulation of the expression and of the secretion of mediators contained therein (Facci L. et al. Proc. Natl. Acad. Sci. U.S.A. 1995, 92: 3376–3380). It is also known that the functional activation of the CB1 receptor by N-acylvanillin amide molecules reduces the sensitization induced by NGF on specific cell lines which coexpress the cannabinoid CB1 receptor (Bisogno T. et al. 1998 Patent No. MI98A002064). It has also been shown that this desensitization depends on an inhibitory modulation of the levels of trk receptor expressed by the specific cell lines by the above-mentioned N-acylvanillin amide molecules (De Marzo et al. PNAS 1999, submitted). These N-acylvanillin amide molecules, which are functional agonists of the CB1 receptor, given their chemical construction, also bring about a functional occupation of the vanilloid receptor VR which results in a significant strengthening of the NGF desensitizing effect brought about by the functional activation of the CB1 receptor by means of N-acylvanillin amide (Di Marzo et al PNAS, 1999, submitted).

Up to now, neither the activity of molecules functionally agonistic to the CB2 receptor and of molecules functionally agonistic to the CB1 receptor, nor the synergy between these actions at the level of the interactions between mast cells and the Th2 lymphocytes resulting from the stimulation induced by the viral protein gp120 on the mast cell has been known. It has recently been discovered that molecules with an N-acylvanillin amide-type structure which have been found to be capable of acting as functional agonists of the peripheral cannabinoid receptor CB1, have strongly synergic activity with molecules which can act as functional agonists of the CB2 receptor expressed by the mast cell (Bisogno T. et al. Italian patent application No. MI98A002064), such as the molecules discovered by the inventors of this patent.

It is also known that the bioavailability of compounds with poor solubility both in an aqueous environment and in a lipid environment—an essential element for the purposes of the manifestation of a biologically important effect—is often very limited and variable and in any case such as to constitute a problem to be evaluated with care with a view to their use for therapeutic purposes.

Bioavailability is in fact influenced by various factors and, in the first place, by the chemical and physical characteristics of the compound. The size of the molecule, its charge, its ability to bind to or mix with endogenous compounds such as biliary salts, plasma proteins or plasma or lymphatic lipids, its stability in the acid pH of the gastric juices are, for example, among the factors which may greatly influence the bioavailability of a compound.

More generally, a certain degree of solibility in an aqueous medium favours both their rapid dissolving in the biological fluids and their subsequent contact with the cell membranes, through which they then diffuse as a result of active or passive transportation processes; water-solubility alone, however, does not per se ensure optimal bioavailability.

In order to achieve this object, a compound must also have certain degree of lipo-solubility to enable it to have an efficient interaction with the cell plasma membranes which constitute barriers to be crossed by passive diffusion. In fact, since, in the tissues, there is a system of "solvents" formed by lipids of the cell membranes and by the interstitial and cytoplasmic liquids, absorption represents an extremely complex process which is dependent on the chemical and physical characteristics of the compound; although, on the one hand, lip-solubility favours the passage of the compound through the cell membranes, on the other hand, this passage is controlled and is dependent proportionally on the concentration of the compound in the aqueous phase, which is also partly correlated with its ability to ionize in a physiological medium.

SUMMARY OF THE INVENTION

The inventors of the present patent application have now found that novel covalent derivatives of alkanolamides of monocarboxylic and dicarboxylic acids with aminoalcohols can usefully be used as drugs with lipid/water partition coefficients and/or with solubility levels which are clearly favourable to interaction with biological membranes. In the novel covalent derivatives of the invention, which have been found to be surprisingly stable, the hydrogen of the alcoholic residue of the alkanolamine is substituted by specific groups which can give a covalent bond with the oxygen.

The novel drugs have been found to be functionally active, as such, on the CB2 cannabinoid receptor, whereas they are inactive on the CB1 receptor. A clear synergy of action between the said compounds and molecules of an N-acylvanillin amide character which are functionally active on the CB1 receptor has also been shown.

A further subject of the present invention is the use of the above-mentioned novel covalent compounds—alone or in association with N-acylvanillin amide molecules active on the peripheral CB1 receptor—for the preparation of pharmaceutical compositions for human and veterinary use, which are effective for the treatment of the following pathological conditions: immuno-inflammatory conditions of various tissue regions, neurodegenerative conditions, conditions due to the spread of opportunistic viruses, as well as pathological conditions in which a non-psychomimetic effect of cannabinoids is noted; and their compositions for administration by various routes, including the parental, endovenous, intramuscular and subcutaneous routes, the gastroenteric route, the topical skin and muscous-membrane routes, and transdermal, ophthalmic and naso-pulmonary routes.

DETAILED DESCRIPTION OF THE INVENTION

The present invention relates to compounds of the general formula (I):

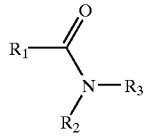

(I)

their enantiomers, diastereoisomers, racemates and mixtures thereof, in which:

(a) R1 may be (1) a linear or branched alkyl radical, saturated or with from 1 to 6 double bonds, a monocylic or polycyclic alkyl or alkenyl radical, or an aryl, arylalkyl or heterocyclic radical having one or more heteroatoms, the radicals optionally being substituted with one or more groups selected from hydroxy, acylamide, keto, nitro, alkoxy, halogen, mercapto, alkylthio, alkyldithio or aryldithio, —N$^+$R7R8R9 Z$^-$, in which R7, R8 and R9 are identical to one another or different and may be alkyl, alkenyl or arylalkyl radicals and Z$^-$ is the anion of a pharmaceutically acceptable organic or inorganic acid;

(2) a group of formula (II):

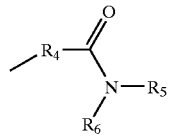

(II)

in which R4 is a linear or branched alkylene radical saturated or with from 1 to 6 double bonds, a cycloalkylene or cycloalkylene radical, or an aryl, arylalkyl or heterocyclic diradical with one or more heteroatoms, the radicals optionally being substituted with one or more groups selected from hydroxy, acylamide, keto, nitro, alkoxy, halogen, mercapto, alkylthio, alkyldithio, or aryldithio, R5 and R6 have the meanings given below for R2 and R3, respectively, or R5 is a group of formula —Y—OH, where Y has the meaning described below in point (c);

(3) a group of formula (III);

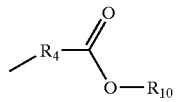

(III)

in which R4 has the meanings described above and R10 is hydrogen or a linear or branched alkyl radical or an arylalkyl radical, in which, when R10 is hydrogen, the resulting carboxylic group may optionally be salified with an organic or inorganic base to form a pharmaceutically acceptable salt;

(b) R2 is selected from hydrogen or an alkyl, alkenyl or arylalkyl radical;

(c) R3 is a group of formula (IV):

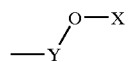

(IV)

in which:

Y is a linear or branched alkyl radical, optionally substituted with one or more phenyl groups, possibly substituted with one or more hydroxy and/or alkoxy groups;

X is selected from:

(1) the radical of a cycloalkyl-ether or cycloalkylthio-ether with a ring of from 3 to 7 members, possibly substituted and possibly comprising a second heteroatom;

(2) a group of formula (V):

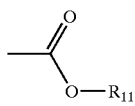

(V)

in which R11 is selected from: a linear or branched alkyl or alkenyl radical, possibly containing for 1 to 5 heteroatoms, which may be identical to one another or different, a monocyclic or polycyclic alkyl radical, an arylalkyl radical, an aryl radical or a heterocyclic radical which is aromatic or completely or partially saturated, having one or more heteroatoms, the radicals optionally being substituted with one or more groups selected from hydroxy, amino, acylamino, keto, ureide, guanidino, nitro, alkoxy, halogen, —O—PO$_3$H$_2$, —O—PO$_2$H$_2$, —O— SO$_3$H, —SO$_3$H, mercapto, alkylthio, alkyldithio, aryldithio, azido, —NHR9, —NR7R8, —N$^+$R7R8R9 Z$^-$, in which Z$^-$ is the anion of a pharmaceutically acceptable organic or inorganic acid and R7, and R8 and R9 are as defined above, or R7 and R8 may form, together with the nitrogen atom to which they are found, a ring of from 3 to 7 members, possibly containing other heteroatoms selected from oxygen, sulphur and nitrogen, the nitrogen possibly being substituted by an alkyl, benzyl or hydroxyethyl radical, and in which the basic and acid groups present in the molecule may possibly be salified with organic or inorganic acids and bases, respectively, to form pharmaceutically acceptable salts;

(3) a group of formula (VI):

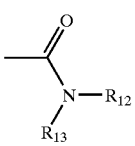

(VI)

in which:

(i) R12 is selected from: a linear or branched alkyl or alkenyl radical possibly containing from 1 to 5 heteroatoms which may be identical to one another or different, a monocylic or polycyclic alkyl radical, an arylalkyl radical, an aryl radical or a heterocyclic radical which is aromatic, or completely or partially saturated, having one or more heteroatoms, the radicals optionally being substituted with one or more groups selected from hydroxy, amino, acylamino, keto, ureide, guanidino, nitro, alkoxy, —O—C$_4$H$_4$—W, halogen, —O—PO$_3$H$_2$, —O—PO$_2$H$_2$, —O—SO$_3$H, —SO$_3$H, mercapto, alkylthio, alkyldithio, aryldithio, azido, —NHR9, —NR7R8, —N$^+$R7R8R9 Z$^-$, in which Z$^-$ is the anion of a pharmaceutically acceptable organic or inorganic acid, and R7, R8 and R9 are as defined above or R7 and R8 may form, together with the nitrogen atom to which they are bound, a ring of from 3 to 7 members, possibly containing other heteroatoms selected from oxygen, sulphur and nitrogen, possibly substituted with an alkyl, benzyl or hydroxyethyl radical, in which W is selected from hydrogen, alkyl, alkoxy, nitro, halogen and hydroxy, and in which the basic and acid groups present in the molecule may possibly be salified with organic or inorganic acids and bases, respectively, to form pharmaceutically acceptable salts; and R13 has, independently, the meanings of R12, or may be hydrogen;

(4) a group of formula (VII):

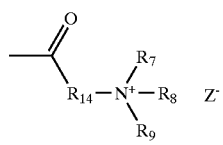

(VII)

in which R14 is selected from: a linear or branched alkylene or arylalkylene radical, possibly substituted with a hydroxy group or —O—CO—R15, in which R15 is an alkyl, alkenyl or arylalkyl radical, R7, R8 and R9 are as defined above, or R7 and R8 may form, together with the nitrogen atom to which they are bound, a ring of from 3 to 7 members as defined above, and $Z^-$ is a pharmaceutically acceptable inorganic or organic anion;

(5) a group of formula (VIII):

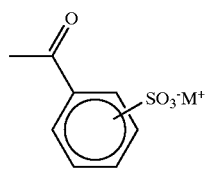

(VII)

in which the —$SO_3^-$ group may be in the ortho, meta or para position relative to the keto group, and $M^+$ is a pharmaceutically acceptable inorganic or organic cation.

If R2 and R5 are both present on the same molecule, they are preferably identical to one another.

If R3 and R6 are both present on the same molecule, they are preferably identical to one another.

When R1 is an alkyl radical, it is preferably saturated or mono-unsaturated. It preferably has from 1 to 23 carbon atoms, more preferably from 11 to 17 carbon atoms and even more preferably from 13 to 15 carbon atoms.

When R4 is an alkylene radical, it is preferably saturated or mono-unsaturated. It preferably has from 1 to 20 carbon atoms, even more preferably from 6 to 14 carbon atoms.

When R7, R8 or R9 is an alkyl or alkenyl radical, it preferably has from 1 to 7 carbon atoms. Even more preferably R7, R8 and R9 are identical to one another and are methyl groups.

When R10 is an alkyl radical, it preferably has from 1 to 20 carbon atoms.

When R10 is hydrogen and the resulting carboxyl group is salified, it is preferably a lithium, sodium potassium, calcium, magnesium, zinc, copper, ammonium, or mono-, di- tri- o tetra-alkyl ammonium salt. In the latter case, preferred bases for the salification are mono-ethanolamine, N-(2-hydroxyethyl)dimethyl ammonium, choline or amino-acids amongst which lysine is preferred.

When R2 is an alkyl or alkenyl group, it preferably has from 1 to 7 carbon atoms.

When Y is an alkylene radical, it preferably has from 2 to 20 carbon atoms, even more preferably from 2 to 6 carbon atoms.

When X is a cycloalkyl-ether or a thio-ether, it preferably has a ring with 5 or 6 members, even more preferably, it is selected from tetrahydropyran-2-yl, tetrahydrofuran-2-yl, tetrahydrothiopyran-2-yl, tetrahydrothiofuran-2-yl, 4-methoxytetrahydropyran-2-yl, or 1,4-dioxan-2-yl.

When R11 or R12 is an alkyl or alkenyl radical, it preferably has from 1 to 25 carbon atoms.

When R11 or R12 is an alkyl or alkenyl radical containing from 1 to 5 heteroatoms, these heteroatoms are preferably selected from sulphur, oxygen and nitrogen.

When R7 and R8 form, together with the nitrogen atoms to which they are bound, a ring, the ring preferably has from 5 to 7 members. When the ring contains a further nitrogen atom and this nitrogen atom is substituted by an alkyl radical, it is preferably a methyl or an ethyl group.

When the —NR12R13 group is the residue of a cyclic amine, this amine is preferably selected from piperidine, pyrrolidine, morpholine, piperazine and hydroxyethylpiperazine.

When R14 is an alkylene radical, it preferably has from 1 to 10 carbon atoms, more preferably from 2 to 4 carbon atoms.

When R15 is an alkyl or alkenyl radical, it preferably has from 1 to 7 carbon atoms.

$Z^-$ to preferably selected from chloride, bromide, sulphate, methane sulphonate, hydrogen phosphate, benzene sulphonate, p-toluene sulphonate, acetate, succinate and benzoate.

$M^+$ is preferably selected from the following cations: lithium, sodium, potassium, calcium, magnesium, zinc, copper, ammonium, mono-, di-, tri- or tetra-alkyl ammonium, more preferably monoethanol ammonium, N-(2-hydroxyethyl) dimethyl ammonium, or cations of choline or of an amino-acid, preferably lysine.

The term "acylamino" preferably means an acetylamino group.

The term "alkoxy" preferably means a methoxy group.

The term "halogen" preferably means chloro, bromo, iodo or fluoro.

The term "pharmaceutically acceptable acid" preferably means an acid selected from hydrochloric, sulphuric, phosphoric, methane sulphonic, benzene sulphonic, p-toluene sulphonic, acetic, succinic and benzoic acid.

The term "pharmaceutically acceptable base" preferably means a base which can form a lithium, sodium, potassium, calcium, magnesium, zinc, copper, ammonium, or mono-, di-, tri- or tetra-alkyl ammonium salt. In the latter case the base is preferably monoethanolamine, N-(2)-hydroxyethyl) dimethyl amine, choline or an amino-acid most preferably lysine.

The term "arylalkyl radical" preferably means a $C_7$–$C_{10}$ arylalkyl radical, more preferably a benzyl group.

The term "aryl radical" preferably means a $C_6$–$C_{10}$ aryl radical, more preferably a phenyl group.

The term "heterocyclic radical" preferably means the radical of a saturated, unsaturated or aromatic heterocycle with a ring having 5 or 6 members, more preferably selected from tetrahydrofuran, tetrahydropyran, dioxane, pyrrolidine, piperidine, morpholine, thiomorpholine, piperazine, N-methylpiperazine, pyrrole, thiophene, furan, pyrazole, imidazole, thiazole, tetrazole, pyridine, pyrazine, pyrimidine, pyridazine, quinoline, isoquinoline, indole, benzoimidazole, benzothiazole.

The term "cycloalkyl radical" or "cycloalkenyl radical" preferably means a ring with from 3 to 10 carbon atoms, more preferably 5 to 6 carbon atoms,

PREPARATION OF THE COMPOUNDS OF THE INVENTION

The compounds of the invention may be prepared by reaction an intermediate of formula (Ia):

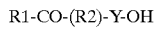   (Ia)

in which R, R2 and Y are as defined above, with a compound of formula X', where X' is selected from:

   (IIa)

in which n is 0 or a whole number between 1 and 4,;
and iodo and R11 is as defined above;
R12—N=C=O or R12R13N-CO-Alg, in which R12, R13 and Alg are as defined above;
Alg-CO-R14-N$^+$R7R8RR9 Z$^-$, in which R7, R8, R9, R14, Z$^-$ and Alg are as defined above; and
Alg-CO-Ph-SO$_3^-$ M$^+$, in which M$^+$ and Alg are as defined above.

The reaction for the condensation of the intermediates of formula (Ia) with the compounds X' is generally carried out in an inert solvent and preferably at a temperature of between −10° C. and the boiling point of the solvent used.

An organic base such as, for example, a tertiary amine, or an inorganic base such as a carbonate or a bicarbonate of an alkali-metal or alkaline-earth metal may also advantageously be used.

Alternatively, when the compound X' contains a carbonyl group which is intended to react with the hydroxyl group of the intermediate (Ia), this carbonyl group may be activated for condensation in known manner, for example, by transforming it into a hydroxysuccinimide ester or into a mixed anhydride, or by carrying out the condensation reaction in the presence of a condensing agent such as a carbodiimide.

The compounds X' are known and/or commercially available or may be prepared from known and/or commercially available products in accordance with methods well known to an expert in the art.

The compounds of formula (Ia) can be prepared as described in EP 0 550 008, EP 0 550 006 and EP 0 570 714 which are incorporated herein by reference.

The preparation of the compounds of formula (I) is further described by the following preparation examples.

EXAMPLE 1

Preparation of N-[2-(ethoxycarbonyl)oxyethyl] hexadecanamide (PEA-EC)

3.0 g of N-(2-hydroxyethyl) hexadecanamide (10 mmoles) was dissolved in 75 ml of tetrahydrofuran (THF) at 45° C. with stirring. 1.11 g of N-methylmorpholine (11 moles) and 1.19 g of ethyl chloroformate (11 moles) were added and the resulting mixture was stirred for a further 3 hours at ambient temperature. The mixture was then evaporated to dryness under vacuum. The residue was taken up with 50 ml of water and extracted 3 times with 30 ml of ethyl acetate; the organic phases were washed twice with 20 ml of water, recombined and evaporated to dryness. The residue was crystallized from 30 ml of tert-butylmethyl ether. The crystallizate was separated by filtration, washed twice with 5 ml of cold tert-butylmethyl ether and finally dried under a high degree of vacuum. The yield of the reaction was 93%.

The product N-[2-ethoxycarbonyl)oxyethyl] hexadecanamide had the following chemical and physical characteristics:

| | |
|---|---|
| empirical formula: | C$_{21}$H$_{41}$NO$_4$ |
| formula weight: | 371.57 |
| elemental composition: | C = 67.88%; H = 11.12%; N = 3.77%, O = 17.22% |
| solubility in water: | slightly soluble |
| solubility in organic solvents: | 10 mg/ml in ethanol, ethyl acetate and n-octanol |
| melting point: | 71–73° C. |
| TLC in 100% ethyl acetate: | Rf = 0.62 |
| TLC in heptane/isopropanol/ ethyl acetate/water (40:20:50:2): | Rf = 0.70 |

EXAMPLE 2

Preparation of N-[2-(isobutyloxycarbonyl)oxyethyl] hexadecanamide (PEA-IBC)

3.0 g of N-[2-hydroxyethyl)hexadecanamide (10 mmoles) was dissolved in 75 ml of tetrahydrofuran (THF) at 45° C. with stirring. 1.11 g of N-methylmorpholine (11 mmoles) and 1.502 g of isobutyl chloroformate (11 mmoles) were added and the resulting mixture was stirred for a further 3 hours at ambient temperature. The mixture was then evaporated to dryness under vacuum. The residue was taken up with 50 ml of water and extracted 3 times with 30 ml of ethyl acetate; the organic phases were washed twice with 20 ml of water, recombined and evaporated to dryness. The residue was crystallized from 30 ml of cold tert-butylmethyl ether and finally dried in a high degree of vacuum. The yield of the reaction was 50%.

The product, N-[2-(isobutyloxycarbonyl)oxyethyl hexadecanamide had the following chemical and physical characteristics:

| | |
|---|---|
| empirical formula: | C$_{23}$H$_{45}$NO$_4$ |
| formula weight: | 399.62 |
| elemental composition: | C = 69.13%; H = 11.35%; N = 3.50%; O = 16.02% |
| solubility in water: | slightly soluble |
| solubility in organic solvents: | 1 mg/ml in ethyl acetate, 10 mg/ml in ethanol, and n-octanol, hot |
| melting point: | 65–67° C. |
| TLC in 100% ethyl acetate: | Rf = 0.66 |
| TLC in heptane/isopropanol/ ethyl acetate/water (40:20:50:2): | Rf = 0.73 |

EXAMPLE 3

Preparation of N-[3-(ethoxycarbonyl)oxypropyl] hexadecanamide (PPA-EC)

3.14 g of N-(3-hydroxypropyl) hexadecanamide (10 mmoles) was suspended in 75 ml of tetrahydrofuran (THF) at 45° C. with stirring. 1.11 g of N-methylmorpholine (11 mmoles) and 1.19 g of ethyl chloroformate (11 mmoles) were added and the resulting mixture was stirred for a further 3 hours at ambient temperature. The mixture was then evaporated to dryness under vacuum. The residue was taken up with 50 ml of water and extracted 3 times with 30 ml of ethyl acetate; the organic phases were washed twice with 20 ml of water, recombined and evaporated to dryness. The residue was crystallized from 30 ml of tert-butylmethyl ether. The crystallizate was separated by filtration, washed twice with 5 ml of cold tert-butylmethyl ether and finally dried in a high degree of vacuum. The yield of the reaction was 92%.

The product, (N-[3-)ethoxycarbonyl)oxypropyl] hexadecanamide had the following chemical-physical characteristics:

| | |
|---|---|
| empirical formula: | $C_{22}H_{43}NO_4$ |
| formula weight: | 385.59 |
| elemental composition: | C = 68.53%; H = 11.24%; N = 3.63%; O = 16.60% |
| solubility in water: | slightly soluble |
| solubility in organic solvents: | 10 mg/ml in ethanol, ethyl acetate and n-octanol |
| melting point: | 66–68° C. |
| TLC in 100% ethyl acetate: | Rf = 0.61 |
| TLC in heptane/isopropanol/ethyl acetate/water (40:20:50:2): | Rf = 0.68 |

EXAMPLE 4

Preparation of N,N¹-bis[2-(ethoxycarbon)oxyethyl] nonandiamide (ADM-EC)

1.37 g of N,N¹-bis(2-hydroxyethyl) nonandiamide (5 mmoles) was dissolved in 20 ml of anhydrous pyridine. The solution was cooled to 4° C. and supplemented with 1.19 g of ethyl chloroformate (11 mmoles); the resulting mixture was stirred for 1 hour at 4° C. and then for 3 hours at ambient temperature. The mixture was then evaporated to dryness under vacuum. The residue was taken up with 50 ml of water and extracted 3 times with 30 ml of ethyl acetate; the organic phases were washed twice with 10 ml of water, recombined and evaporated to dryness. The residue was crystallized twice, first from 20 ml of ethyl acetate and then from 20 ml of tert-butylmethyl ether. The crystallizate was separated by filtration, washed twice with 5 ml of cold tert-butylmethyl ether, and finally dried in a high degree of vacuum. The yield of the reaction was 88%.

The product, N,N¹-bis[2-(ethoxycarbonyl)oxyethyl] nonandiamide had the following chemical and physical characteristics:

| | |
|---|---|
| empirical formula: | $C_{19}H_{34}N_2O_8$ |
| formula weight: | 418.5 |
| elemental composition: | C = 54.53%; H = 8.19%; N = 6.69%; O = 30.59% |
| solubility in water: | slightly soluble |
| solubility in organic solvents: | 10 mg/ml in ethanol, DMSO |
| melting point: | 78–80° C. |
| TLC in 100% ethyl acetate: | Rf = 0.75 |
| TLC in toluene/ethanol/acetic acid (63:30:5): | Rf = 0.52 |

EXAMPLE 5

Preparation of N-[2-benzylaminocarbonyl)oxyethyl] hexadecanamide (PEA-BCM)

3.0 g of N-(2-hydroxyethyl) hexadecanamide (10 moles) was suspended in 60 ml of anhydrous toluene; the mixture was stirred and heated with refluxing of the solvent into anhydrous 4 Å molecular sieves with recycling. 3.0 ml of benzylisocyanate was added and the resulting mixture was heated with refluxing for 6 hours. 2 ml of methanol was then added and the heating to temperature was continued for a further hour. The product crystallized as a result of cooling to ambient temperature. The crystallizate was separate by filtration, washed twice with 5 ml of cold toluene and finally dried under a high degree of vacuum. The yield of the reaction was 94%.

The product, N-[2-benzylaminocarbonyl)oxyethyl] hexadecanamide had the following chemical and physical characteristics:

| | |
|---|---|
| empirical formula: | $C_{16}H_{44}N_2O_3$ |
| formula weight: | 432.65 |
| elemental composition: | C = 72.18%; H = 10.25%; N = 6.48%; O = 11.09% |
| solubility in water: | slightly soluble |
| solubility in organic solvents: | 10 mg/ml in ethyl acetate and n-octanol, hot |
| melting point: | 126.5–128.5° C. |
| TLC in 100% ethyl acetate: | Rf = 0.47 |
| TLC in heptane/isopropanol/ethyl acetate/water (40:20:50:2): | Rf = 0.65 |

EXAMPLE 6

Preparation of N-[2-(ethoxycarbonylmethyl) aminocarbonyl]oxyethyl] hexadecanamide (PEA-EGC)

3.0 g of N-(2-hydroxyethyl) hexadecanamide (10 mmoles) was suspended in 60 ml of anhydrous toluene; the mixture was stirred and heated with refluxing of the solvent onto 4 Å molecular sieves with recycling. 3.0 g of ethyl isocyanate acetate was added and the resulting mixture was heated with refluxing for 6 hours. The mixture was then cooled to 4° C. The crystallizate formed was separated by filtration and crystallized from 20 ml of toluene, cold; it was then separated again by filtration, washed twice with 5 ml of cold toluene and finally dried in a high degree of vacuum. The yield of the reaction was 92%.

The product, N-[2-[(ethoxycarbonylmethyl) aminocarbonyl]oxyethyl] hexadecanamide had the following chemical and physical characteristics:

| | |
|---|---|
| empirical formula: | $C_{23}H_{44}N_2O_5$ |
| formula weight: | 428.62 |
| elemental composition: | C = 64.45%; H = 10.35%; N = 6.54%; O = 18.66% |
| solubility in water: | slightly soluble |
| solubility in organic solvents: | 10 mg/ml in ethanol, n-octanol, hot |
| melting point: | 105–106° C. |
| TLC in 100% ethyl acetate: | Rf = 0.40 |
| TLC in heptane/isopropanol/ethyl acetate/water (40:20:50:2): | Rf = 0.58 |

EXAMPLE 7

Preparation of N-[2-[(2-piperidinoethoxy)carbonyl] oxyethyl] hexadecanamide (PEA-PEC)

3.0 g of N-(2-hydroxyethyl) hexadecanamide (10 mmoles) was dissolved in 60 ml of tetrahydrofuran (THF) in an anhydrous N$_2$ atmosphere. 1.11 g of N-methylmorpholine (11 mmoles) was added and the mixture was further supplemented with 1.88 g of (2-bromoethyl) chloroformate (10 mmoles) slowly, dropwise, over a period of 30 minutes. The resulting mixture was kept at ambient temperature with stirring for a further 3 hours and then evaporated to dryness. The residue was taken up with 20 ml of water and extracted 3 times with 20 ml of ethyl acetate. The organic phases were washed twice with 20 ml of water, recombined and evaporated to dryness. The residue was taken up with 50 ml of anhydrous tetrahydrofuran and supplemented with 1.70 g of piperidine (20 mmoles). The mixture was heated to reflux with stirring for 6 hours; it was then cooled to ambient temperature and supplemented with 20 ml of water and 60 ml of ethyl acetate. The aqueous phase was discarded the organic phase was washed with 10 ml of cold 2M NH$_3$ solution and then with 20 ml of cold water. The aqueous phases were discarded and the organic phase was evaporated to dryness. The residue was crystallized from 30 ml of ethyl acetate, cold. The crystallizate was separated by filtration, washed twice with 5 ml of cold ethyl acetate and finally dried under a high degree of vacuum. The yield of the reaction was 89%.

The product, N-[2-[(2-piperidinoethoxy)carbonyl] oxyethyl] hexadecanamide had the following chemical and physical characteristics:

| | |
|---|---|
| empirical formula: | C$_{26}$H$_{50}$N$_2$O$_4$ |
| formula weight: | 454.70 |
| elemental composition: | C = 68.68%; H = 11.08%; N = 6.16%; O = 14.08% |
| solubility in water: | slightly soluble |
| solubility in organic solvents: | 10 mg/ml in ethanol, |
| melting point: | 65–67° C. |
| TLC in 100% ethyl acetate: | Rf = 0.05 |
| TLC in toluene/ethanol/ acetate acid (65:30:5): | Rf = 0.11 |

EXAMPLE 8

Preparation of N-[2-[(2-piperidinoethoxy)carbonyl] oxyethyl] hexadecanamide methane sulphonate (PEA-PECMetS)

4.5 g of N-[2-[(2-piperidinoethoxy)carbonyl]oxyethyl] hexadecanamide was dissolved in 50 ml of anhydrous ethanol and supplemented with 0.96 g of methane sulphonic acid, cold. The mixture was evaporated to dryness and the residue was taken up with 100 ml of distilled water. The solution was frozen and lyophilized.

The product, N-[2-[(2-piperidinoethoxy)carbonyl] oxyethyl] hexadecanamide methane sulphonate had the following chemical and physical characteristics:

| | |
|---|---|
| empirical formula: | C$_{27}$H$_{54}$N$_2$O$_7$S |
| formula weight: | 550.82 |
| elemental composition: | C = 58.88%; H = 9.88%; N = 5.09%; O = 20.23% S = 5.82% |
| solubility in water: | 10 mg/ml |
| solubility in organic solvents: | 10 mg/ml in ethanol and DMSO |
| melting point: | n.d. |
| TLC in toluene/ethanol/ acetic acid (65:30:5): | Rf = 0.11 |

EXAMPLE 9

Preparation of the tetrahydrofuranyl ether of N-(2-hydroxyethyl) hexadecanamide (PEA-THF)

3.0 g of N-(2-hydroxyethyl) hexadecanamide (10 mmoles) was suspended in 20 ml of 2,3-dihydrofuran and cooled to 4° C. The mixture was supplemented with 200 mg of pyridinium methane sulphonate with continuous stirring and then heated to 50° C. for 60 minutes. The mixture was brought to ambient temperature, supplemented with 50 ml of ethyl acetate and extracted twice with 10 ml of cold water. The aqueous phases were separated and discarded and the organic phase was evaporated to dryness under vacuum. The residue was crystallized from 20 ml of tert-butylmethyl ether. The crystallizate was separated by filtration, washed twice with 4 ml of cold tert-butylmethyl ether and finally dried under a high degree of vacuum. The yield of the reaction was 90%.

The product, the tetrahydrofuranyl ether of N-(2-hydroxyethyl) hexadecanamide had the following chemical and physical characteristics:

| | |
|---|---|
| empirical formula: | C$_{22}$H$_{43}$NO$_3$ |
| formula weight: | 369.59 |
| elemental composition: | C = 71.50%; H = 11.73%; N = 3.97%; O = 12.99% |
| solubility in water: | slightly soluble |
| solubility in organic solvents: | 10 mg/ml in ethanol and DMSO |
| melting point: | 63–65° C. |
| TLC in 100% ethyl acetate: | Rf = 0.41 |
| TLC in heptane/isopropanol/ ethyl acetate/water (40:20:50:2): | Rf = 0.62 |

EXAMPLE 10

Preparation of the tetrahydrofuranyl ether of N,N$^1$-bis(2-hydroxyethyl) nonandiamide (ADM-THF)

1.37 g of N,N$^1$-bis (2-hydroxyethyl) nonandiamide (5 mmoles) was suspended in 6ml of 2,3-dihydrofuran. The mixture was stirred at 4° C. and supplemented with 60 mg of pyridinium methane sulphonate; the mixture was then heated to 50° C. for 60 minutes. The mixture was then cooled to ambient temperature, supplemented with 30 ml of ethyl acetate and extracted twice with 5 ml of cold water. The aqueous phases were separated and discarded and the organic phases were evaporated to dryness under vacuum. After thorough drying in a high degree of vacuum, the residue was dispersed cold with 5 ml of tert-butylmethyl ether. The powdery solid thus obtained was separated by filtration, washed twice with 2 ml of cold tert-butylmethyl ether and finally dried under a high degree of vacuum. The yield of the reaction was 94%.

The product, the tetrahydrofuranyl ether of N,N$^1$-bis(2-hydroxyethyl) nonandiamide had the following chemical and physical characteristics:

| | |
|---|---|
| empirical formula: | C$_{21}$H$_{38}$N$_2$O$_6$ |
| formula weight: | 414.55 |
| elemental composition: | C = 60.84%; H = 9.24%; N = 6.76%; O = 23.16% |
| solubility in water: | 10 mg/ml in water |
| solubility in organic solvents: | 10 mg/ml in ethanol and DMSO |
| melting point: | 58–60° C. |
| TLC in acetonitrile/water (9:1): | Rf = 0.52 |
| TLC in toluene/ethanol/ acetic acid (65:30:5): | Rf = 0.44 |

EXAMPLE 11

Preparation of the tetrahydropyranyl ether of N-(2-hydroxyethyl) hexadecanamide (PEA-THP)

3.0 g of N-bis(2-hydroxyethyl) hexadecanamide (10 mmoles) was suspended in 20 ml of 3,4-dihydropyran and cooled to 4° C. 200 mg of pyridinium methane sulphonate was added and the mixture was stirred at 50° C. for 60 minutes. The mixture was then brought to ambient temperature, supplemented with 50 ml of ethyl acetate and extracted twice with 10 ml of cold water. The aqueous phases were separated and discarded and the organic phase was evaporated to dryness with rotation. The residue was taken up with 20 ml of petroleum ether and crystallized. The crystallizate was separated by filtration, washed twice with 4 ml of cold petroleum ether and finally dried in a high degree of vacuum. The yield of the reaction was 93%.

The product, the tetrahydropyranyl ether of N-(2-hydroxyethyl) hexadecanamide had the following chemical and physical characteristics:

| | |
|---|---|
| empirical formula: | $C_{23}H_{45}NO_3$ |
| formula weight: | 383.62 |
| elemental composition: | C = 70.01%; H = 11.824%; N = 3.65%; O = 12.51% |
| solubility in water: | slightly soluble |
| solubility in organic solvents: | 10 mg/ml in ethyl acetate and n-octanol |
| melting point: | 52.5–54.5° C. |
| TLC in 100% ethyl acetate | Rf = 0.43 |
| TLC in heptane/isopropanol/ ethyl acetate/water (40:20:50:2): | Rf = 0.65 |

EXAMPLE 12

Preparation of the tetrahydropyranyl ether of $N,N^1$-bis(2-hydroxyethyl) nonandiamide (ADM-THP)

1.37 g of $N,N^1$-bis(2-hydroxyethyl) nonandiamide (5 mmoles) was suspended in 6 ml of 3,4-dihydropyran. The mixture was stirred at 4° C. and supplemented with 60 mg of pyridinium methane sulphonate; the mixture was then heated to 50° C. for 60 minutes. The mixture was cooled to ambient temperature, supplemented with 30 ml of ethyl acetate and extracted twice with 5 ml of water. The aqueous phases were separated and discarded and the organic phase was evaporated to dryness under vacuum. After thorough drying in a high degree of vacuum, the residue was dispersed cold with 5 ml of tert-butylmethyl ether. The powdery solid thus obtained was separated by filtration, washed twice with 2 ml of tert-butylmethyl ether and finally dried in a high degree of vacuum. The yield of the reaction was 92%.

The product, the tetrahydropyranyl ether of $N,N^1$-bis(2-hydroxyethyl) nonandiamide had the following chemical-physical characteristics:

| | |
|---|---|
| empirical formula: | $C_{23}H_{42}N_2O_6$ |
| formula weight: | 442.60 |
| elemental composition: | C = 62.42%; H = 9.57%; N = 6.33%; O = 21.69% |
| solubility in water: | 10 mg/ml |
| solubility in organic solvents: | 10 mg/ml in ethanol and DMSO |
| melting point: | 55–57° C. |
| TLC in acetonitrile (9:1): | Rf = 0.56 |
| TLC in toluene/ethanol/ acetic acid (65:30:5): | Rf = 0.51 |

EXAMPLE 13

Preparation of N-[2-(ethoxycarbonyl)oxyethyl] oleoylamide (OEA-EC)

3.3 g of N-(2-hydroxyethyl) oleoylamide (10 mmoles) was dissolved in 75 ml of tetrahydrofuran (THF) with stirring. The solution was cooled to 4° C. and supplemented with 1.11 g of N-methyl morpholine (11 mmoles) and 1.19 g of ethyl chloroformate (11 mmoles). The resulting mixture was kept at 4° C. for 30 minutes with continuous stirring and then for a further 24 hours at ambient temperature. The mixture was then evaporated to dryness under vacuum. The residue was taken up with 50 ml of water and extracted 3 times with 30 ml of ethyl acetate; the organic phases were washed twice with 20 ml of water, recombined and evaporated to dryness. The residue was purified by preparative chromatography on silica gel with the use of a mixture of ethyl acetate and hexane in a ratio of 50:50, as the eluent. The fractions containing the product were recombined and evaporated to dryness. The oily residue was dried under a high degree of vacuum (yield 80%).

The product, N-[2-(ethoxycarbonyl)oxyethyl] oleoylamide had the following chemical and physical characteristics:

| | |
|---|---|
| empirical formula: | $C_{23}H_{43}NO_4$ |
| formula weight: | 397.40 |
| elemental composition: | C = 69.48%; H = 10.90%; N = 3.52%; O = 16.10% |
| solubility in water: | slightly soluble |
| solubility in organic solvents: | 10 mg/ml in ethanol, ethyl acetate and n-octanol |
| TLC in 100% ethyl acetate: | Rf = 0.63 |
| TLC in heptane/isopropanol/ ethyl acetate/water (40:20:50:2): | Rf = 0.69 |

Chemical and physical characteristics of the compounds of the invention

The chemical and physical characteristics of the derivatives according to the invention were evaluated by quantitative according to the invention were evaluated by quantitative measurement of the lipid/water partition parameter.

A useful parameter for evaluating the properties of a compound in relation to its possible absorption is in fact constituted by the coefficient of partition between the lipid phase and the aqueous phase, which is considered to be an expression of its lipophilicity and its degree of hydrophilicity. In general, it is commonly accepted that the greater the lipid/water partition coefficient is, the greater is the affinity for the cell membranes and hence the greater and quicker is the absorption. For the purpose of evaluating the characteristics of the derivatives of the invention, the partition parameter RM between the lipid and the aqueous phase, extrapolated from thin-film partition chromatography, was calculated; this parameter is commonly used to evaluate the lipophilic characteristics of compounds (Tomlinson E. J. Chromatogr. 1975, 113, 1) and is commonly used, for example, for local anaesthetics, in which a correlation has been shown between this parameter and biological activity (Bachrata M. et al. J. Chromatogr. 1979, 171, 29–36).

The partition parameter RM between the lipid phase and the aqueous phase was calculated both for the derivatives and for the non-substituted alkanolamides, from the Rf value obtained by thin-film chromatography on silica gel (particles of 2–2.5 µmoles, mean porosity 60 Å, thickness 0.25 mm on glass plate) in accordance with the formula:

RM=log (1/Rf−1)

and the ΔRM was obtained from the difference between the RM coefficients of the derivative and of the corresponding alkanolamide. The results obtained were as follows:

TABLE I

| compound Example No. | solvent 1 | | | solvent 2 | | |
|---|---|---|---|---|---|---|
| | RF | RM | ΔRM | RF | RM | ΔRM |
| 1 | 0.62 | −0.213 | −1.001 | 0.70 | −0.368 | −0.403 |
| 2 | 0.66 | −0.288 | −1.076 | 0.73 | −0.432 | −0.467 |
| 5 | 0.47 | 0.052 | −0.736 | 0.65 | −0.269 | −0.304 |
| 6 | 0.40 | 0.176 | −0.612 | 0.58 | −0.140 | −0.175 |
| 7 | 0.05 | 1.28 | 0.49 | — | — | — |
| 9 | 0.41 | 0.158 | −0.630 | 0.62 | −0.213 | −0.247 |
| 11 | 0.43 | 0.122 | 0.666 | 0.65 | −0.269 | −0.304 |
| 3 | 0.61 | −0.194 | −1.020 | 0.68 | −0.327 | −0.397 |
| 13 | 0.63 | −0.231 | −0.984 | 0.69 | −0.347 | −0.365 |
| 4 | 0.75 | −0.477 | −0.866 | 0.52 | −0.035 | −0.723 |
| 10 | 0.52 | −0.035 | −0.424 | 0.44 | 0.105 | −0.584 |
| 12 | 0.56 | −0.105 | −0.494 | 0.51 | −0.017 | −0.706 |

Solvent 1: 100% ethyl acetate
Solvent 2: heptane:isopropanol:ethyl acetate:H2O 40:20:50:2
Solvent 3: acetonitrile:H2O 9:1
Solvent 4: toluene:ethanol:acetic acid 65:30:5

It can be seen from the results obtained that the covalent derivatives of the present invention surprisingly have a decidedly more marked lipophilic nature than the starting alkanolamides and hence more rapid absorption both at gastrointestinal level and topically. It should also be noted that, as already described in the prior art, substitutions on the alcoholic hydroxyl with carbamates and carbonates have already been investigated in order to improve the water-solubility of "hindered alcohols" but the resulting derivatives were found to be highly unstable (Safadi M. et al. Pharm. Res. 1993, 10, 1350–1355). The derivatives obtained by the invention, on the other hand, have been found, surprisingly, to possess very good lipo-solubility characteristics and have been found to be substantially stable. Water-solubility may, however, also be achieved by introducing substituents which can be ionized and which can thus be salified; compounds with good solubility in aqueous solvents are thus produced, this characteristic being particularly important both for ensuring absorption and for the administration of the pharmacological agent in aqueous solution, for example, by a parenteral route.

The demonstrated ability to substitute the hydrogen of the alcoholic residue of the alkanolamide with novel substituents which can give stable covalent bonds with the oxygen forms part of the present invention.

BIOLOGICAL ACTIVITY OF THE COMPOUNDS OF THE INVENTION

The compounds of the invention were tested with the use of biochemical tests in vitro which are described in the following biological examples. The compounds are identified on the basis of the number of the example given in the preceding chemical examples section above.

Example A

Effect of alkanolamide molecules on the binding of the synthetic ligands of the CB2 and CB1 cannabinoid receptors, respectively.

Rat RBL-2H3+ leukemic basophilic cells, which selectively express the cannabinoid CB2 receptor, and mouse N18TG2 neuroblastoma cells which selectively express the CB1 cannabinoid receptor were used. The cells were cultivated as described above (Facci L. et al. (1995) Proc. Natl: Acad: Sci. U.S.A. 92:: 3376–3380; Bisogno T. et al. 1997 J. Biol. Chem., 272: 3315–3323). WIN 55,212.2 was used as the selectively agonist synthetic ligand for the CB2 receptor.

SR141716A was used as the selective antagonist for the CB1 receptor.

HU-210 was used as the selective antagonist for the CB2 receptor.

[$^3$H]SR141716A (55 Ci/mmol) was supplied by Amersham; [$^3$H]WIN55,212-2 (43 Ci/mmol) was supplied by NEN. The binding tests were performed with membranes of the cells resuspended in 50 mMol Tris pH 7.0 buffer; 2.5 mMol MgCl$_2$, 0.8 mMol EDTA; 0.05% bovine serum albumin (BSA); 0.01% ethanol, in the presence of 100 μM of phenyl-methyl-sulphonyl fluoride (PMSF-Sigma), with the use, of 300 pM of [$^3$H]SR141716A and of [$^3$H]WIN55,212-2, respectively, as the ligand.

The membranes were incubated for 90' at 30° C. and filtered on glass microfibre filters (GFC-Whatman) and the radioactivity was detected by liquid scintillation. The specific binding was calculated with the use of either 10 μM SR141716A or 10 μM HU-210.

The Ki values were calculated by Chang-Prusoff's equation and expressed as concentration μM.

TABLE II

| compounds | CB2 receptor RBL-2H3 + cells Lig. [$^3$H]WIN55, 212-2 Ki (μM) | CB1 Receptor N18TG2 cells Lig. [$^3$H]SR141716A Ki (μM) |
|---|---|---|
| phenyl butazone | >15 | >15 |
| Comp. Example 4 | 0.002 ± 0.0009 | >15 |
| Comp. Example 6 | 0.001 ± 0.0008 | >15 |
| Comp. Example 1 | 0.006 ± 0.0018 | >15 |
| Comp. Example 7 | 0.009 ± 0.0025 | >15 |

Example B

Effect of alkanolamide molecules on the stimulation of cyclic AMP (cAMP) by forskolin.

The tests were performed with the aim of checking whether the binding of the molecules of the present invention to the CB2 receptor has functional significance.

It is in fact known that the function activation of the CB2 receptor brings about, at intracellular level, inhibition of the enzymatic activity of adenylate cyclase and a reduction in the levels of the second-messenger cAMP, resulting in an increase in the conductance of the channels to potassium and an inhibition of proteic phosphorylation (Childers S. R. et al. Biochem. Parmacol. 1996, 52: 819–827).

The dosages of cAMP were performed on RBL-2H3+ cells flowing together in Petri dishes with six wells (Falcon); the cells were stimulated for 10' at 37° C. with 1 μM of forskolin (Fluka) in 400 μl of medium without serum, containing 20 mM HEPES, 0.1 mg/ml BSA and 0.1 mM 1-methyl-3-isobutyl xanthine (Sigma) and either ethanol or alkanolamide molecules with or without the addition of HU-210. After incubation, the cells were extracted and the levels of cAMP were evaluated with a suitable Amersham kit in accordance with the producer's method. The data were expressed in IC50 μM.

TABLE III

| Compounds Example No. | IC50 μM |
|---|---|
| 4 | 1.8 |
| 4 + HU-210 (0.5 μM) | >20 |
| 6 | 1.9 |
| 6 + HU-210 (0.5 μM) | >20 |

The covalent derivatives of the invention can thus usefully be used for the treatment of inflammatory processes, and also those with hyperalgic components—both with a neurogenic basis and with an immunogenic basis—associated with immuno-inflammatory pathological conditions, and also autoimmune conditions, with neurodegenerative conditions associated with excitotoxic processes, as well as for conditions in which a non-psychomimetic effect of cannabinoids is known, all effects being attributable to an activity mediated by the CB2 receptor; amongst these, the following pathological conditions are mentioned by way of non-limiting example: neurological conditions such as, for example, multiple sclerosis, peripheral neuropathies—both somatic and autonomic—with various aetiologies, anoxic-ischaemic strokes and thromboses, cranial and spinal trauma, neurodegenerative conditions (AIDS—complex demetia, senile dementia, Alzheimer's syndrome, Parkinsons syndrome, amyotrophic lateral sclerosis), epilepsy, transitory ischaemic attacks (TIA) Huntington's chorea, retinal conditions with an anoxic-ischaemic basis, and also conditions secondary to glaucoma, headaches; viral conditions with particular reference to conditions sustained by the propagation of so-called opportunistic viruses (such as, for example, the HIV virus), that is, viruses which can use the defense mechanisms of the organism itself to render its own propagation possible; skin conditions such as, for example psoriasis, atopic dermatitis and allergic dermatitis, lichen planus, dermatomyositis, scleroderma, pemphigus, pemphigoids, epidermolysis bullosa, discoid and systemic lupus erythematosus, heliodermatitus, indolent ulcers, hypertrophic scars, keloids, vulvar vestibulitis; conditions of the mucous membrane, such as, for example, oral lichen planus, stomatitis, acute and recurrent vaginitis, balanitis and balanoposthitis, and also conditions connected with inflammatory states of the accessory sex glands (prostate, vesical, seminal, etc.); respiratory conditions such as, for example, asthma, interstitial pulmonary fibrosis, allergic rhinitis; gastrointestinal conditions such as, for example, chronic inflammations of the mucosa, ophthalmic conditions such as, for example uveitis, uveoretinitis, Sjogren's syndrome, keratoconjunctivitis sicca, corneal ulcers, allergic and infectious conjunctivitis and giant papillary conjunctivitis, scar pemphigoids; joint conditions, such as, for example rheumatic arthritis, rheumatoid arthritis, arthritis connected with psoriasis or with lupus, chronic arthritis and arthrosis, chondrodegeneration of traumatic, infectious and degenerative origin; cardiovascular conditions such as, for example, re-stenosis after angioplasty, atherosclerosis and cardiac ischaemic attacks, recurrence of episodes of infarction; specifically veterinary conditions such as, for example, conditions of the intervertebral disks in dogs and in horses, Stringhalt's syndrome, and laminitis in horses, skin, joint or connective-tissue conditions in horses, in dogs and in cats.

For the treatment of the above-mentioned conditions, the derivatives of the present invention may be administered by a parenteral systemic route (endovenously, intramuscularly, subcutaneously), a rectal route, or an oral route but also by a topical route (dermal and mucosal, ophthalmic, naso-pulmonary) and by a transdermal route. The dosages in which they are used may vary according to the administration route and to the seriousness of the disease and of the general condition of the patient. In any case, the expected therapeutic dosages are from 0.1 mg/die to 1 g/die for a period of between one week and three months of continued administration. According to the chronic nature of the condition, the treatment may be repeated in various cycles.

The derivatives according to the invention may be administered in pharmaceutical compositions with excipients or diluents which are acceptable from the point of view of pharmaceutical use and are suitable for the purposes and in any case are such as to permit and/or to optimize adsorption by the selected administration route. In particular, formulations in solution or suspension and also those produced with the use of preliminary micronization techniques and/or co-micronization with other active ingredients or with excipients for parental administration are envisaged; for the ophthalmic route, liquid forms as eye lotions and solid or semisolid forms as inserts, gels and ointments may be selected, and for oral administration they may be in the form of capsules, tablets, powders and pellets and also in gastroresistant formulations and may also be produced with the use of preliminary microencapsulation, liposomization and micellization techniques. For the topical routes, including the transdermal route, formulations as suppositories, micro-enemas, creams, ointments, sprays, gels, foams, dressings of various thicknesses and patches may be used. All of the possible pharmaceutical forms indicated for the various administration routes may also be formulated with excipients or technological processes suitable for producing fast-release or slow-release medicaments which the derivatives of the invention.

It has also been found that the compounds of the present invention may also be used effectively as cosmetic ingredients having the function of conditions and/or rheological additives. A further subject of the present invention is therefore the use of the compounds of formula (I) in cosmetics.

The invention is further described by the following non-limiting examples thereof; it is also possible to use other formulations produced with other ingredients and with other excipients for these purposes.

EXAMPLE 14

Ampoules for Injection

| | |
|---|---|
| Compound of Example 8 | 20 mg |
| sodium chloride | 17 mg |
| water for injectables to make up to | 2 ml |

EXAMPLE 15

Lyophilized Ampoules

| Each lyophilized ampoule contains: | |
|---|---|
| Compound of Example 6 (co-micronized with mannitol) | 30 mg |
| N-(4-hydroxy-3-methoxybenzyl)oleoyl amide (co-micronized with mannitol) | 30 mg |
| mannitol | 80 mg |

-continued

| each solvent ampoule contains: | |
|---|---|
| soya lecithin | 40 mg |
| water for injectables to make up to | 2 ml |

EXAMPLE 16

Tablets

| | |
|---|---|
| Compound of Example 4, micronized | 100 mg |
| lactose | 100 mg |
| maize starch | 70 mg |
| talc | 8 mg |
| magnesium stearate | 4 mg |
| carboxymethyl cellulose | 8 mg |

EXAMPLE 17

Capsules

| | |
|---|---|
| Compound of Example 7 | 100 mg |
| N-(4-hydroxy-3-methoxybenzyl) palmitoylamide | 50 mg |
| maize oil | 150 mg |
| gelatine FU | 70 mg |
| glycerol FU | 30 mg |
| titanium dioxide (E171) | 0.5 mg |
| erythrosin (E127) | 1 mg |

EXAMPLE 18

Eye Lotion

| | |
|---|---|
| Compound of Example 8 | 2 mg |
| benzalkonium chloride | 1 mg |
| monobasic sodium phosphate hydrate | 41 mg |
| dibasic sodium phosphate.12H$_2$O | 249.5 mg |
| sodium edetate | 10 mg |
| bi-distilled water to make up to | 10 ml |

EXAMPLE 19

Ophthalmic Ointment

| | |
|---|---|
| Compound of Example 4, micronized | 100 mg |
| viscous white Vaseline to make up to | 100 g |

EXAMPLE 20

Skin Cream

| | |
|---|---|
| Compound of Example 4 | 100 mg |
| hyaluronic acid | 200 mg |
| sorbitan monostearate | 500 mg |

-continued

| | |
|---|---|
| polyoxyethylene sorbitan monostearate | 3 g |
| stearic acid | 3 g |
| Vaseline oil | 15 g |
| methyl ester of para-oxybenzoic acid | 200 mg |
| ethyl ester of para-oxybenzoic acid | 50 mg |
| demineralized water to make up to | 100 g |

EXAMPLE 21

Vaginal Gel

| | |
|---|---|
| Compound of Example 7 | 150 mg |
| N-(4-hydroxy-3-methoxybenzyl)-palmitoylamide | 100 mg |
| hyaluronic acid, sodium salt | 100 mg |
| sodium alginate | 2.5 g |
| glycerol | 5 g |
| Bronopol | 300 mg |
| demineralized water to make up to | 100 g |

EXAMPLE 22

Lotion for Trichological Use

| | |
|---|---|
| Compound of Example 4 | 300 mg |
| propylene glycol | 25 g |
| ethyl alcohol | 50 g |
| demineralized water to make up to | 100 g |

EXAMPLE 23

Gel for Dental Use

| | |
|---|---|
| Compound of Example 12 | 300 mg |
| hyaluronic acid (titrated in bio-binding epitope) | 200 mg |
| carbomer | 300 mg |
| sorbitol | 20 g |
| methyl p-oxybenzoate | 200 mg |
| ethyl p-oxybenzoate | 50 mg |
| peppermint flavouring | 1 g |
| demineralized water to make up to | 100 g |

What is claimed is:

1. Compounds of the general formula (I):

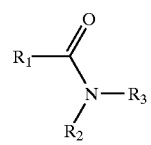

their enantiomers, diastereomers, racemates and mixtures thereof, in which:

(a) R$_1$ is (1) a linear or branched alkyl radical, saturated or with from 1 to 6 double bonds, a monocyclic or polycyclic alkyl or alkenyl radical, or an aryl, arylalkyl or heterocyclic radical having one or more heteroatoms, the radicals optionally being substituted with one or more groups selected from hydroxy, acylamide, keto, nitro, alkoxy, halogen, —N⁺R₇R₈R₉ Z⁻ in which R₇, R₈ and R₉ are identical to one another or different and may be alkyl, alkenyl or arylalkyl radical, and Z⁻ is the anion of a pharmaceutically acceptable organic in inorganic acid;

(2) a group of formula (II):

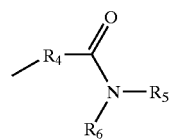

(II)

in which $R_4$ is a linear or branched alkylene radical saturated or with from 1 to 6 double bonds, a cycloalkylene or cycloalkenylene radical, or an aryl, arylalkyl or heterocyclic diradical with one or more heteroatoms, the radicals optionally being substituted with one or more groups selected from hydroxy, acylamide, keto, nitro, alkoxy, halogen, $R_5$ and $R_6$ have the meanings given below for $R_2$ and $R_3$, respectively, or $R_5$ is a group of formula —Y—OH, where Y has the meaning described below in point (c); or (3) a group formula (III):

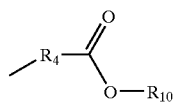

(III)

in which $R_4$ has the meanings described above and $R_{10}$ is hydrogen or a linear or branched alkyl radical or an arylalkyl radical, in which, when $R_{10}$ is hydrogen, the resulting carboxylic group may optionally be salified with an organic or inorganic base to form a pharmaceutically acceptable salt;

(b) $R_2$ is selected from hydrogen or an alkyl, alkenyl or arylalkyl radical;

(c) $R_3$ is group of formula (IV):

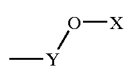

(IV)

in which:

Y is a linear or branched alkyl radical, optionally substituted with one or more phenyl groups, possibly substituted with one or more hydroxy and/or alkoxy groups;

X is selected from:

(1) the radical of a cycloalkyl-ether with a ring of from 3 to 7 members, possibly substituted and possibly comprising a one or two heteroatom;

(2) a group of formula (V):

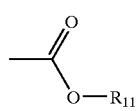

(V)

in which $R_{11}$ is selected from: a linear or branched alkyl or alkenyl radical, possibly containing from 1 to 5 heteroatoms, which may be identical to one another or different, a monocyclic or polycyclic alkyl radical, an arylalkyl radical, an aryl radical or a heterocyclic radical which is aromatic or completely or partially saturated, having one or more heteroatoms, the radicals optionally being substituted with one or more groups selected from hydroxy, amino, acylamino, keto, ureide, guanidino, nitro, alkoxy, halogen, —O—PO₃H₂, —O—PO₂H₂, —O—SO₃H, —SO₃H, azido, —NHR₉, —NR₇R₈, —N⁺R₇R₈R₉ Z⁻, in which Z⁻ is the anion of a pharmaceutically acceptable organic or inorganic acid and R₇, R₈ and R₉ are as defined above or R₇ and R₈ may form, together with the nitrogen atom to which they are bound, a ring of from 3 to 7 members, possibly containing other heteroatoms selected from oxygen and nitrogen, the nitrogen possibly being substituted by an alkyl, benzyl or hydroxyethyl radical, and in which the basis and acid groups present in the molecule may possibly be salified with organic or inorganic acids and bases, respectively, to form pharmaceutically acceptable salts;

(3) a group of formula (VI):

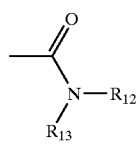

(VI)

in which:

(i) $R_{12}$ is selected from: a linear or branched alkyl or alkenyl radical possibly containing from 1 to 5 heteroatoms which may be identical to one another or different, a mono- or polycyclic alkyl radical, an arylalkyl radical, an aryl radical or a heterocyclic radical which is aromatic or completely or partially saturated, having one or more heteroatoms, the radicals optionally being substituted with one or more groups selected from hydroxy, amino, acylamino, keto, ureide, guanidino, nitro, alkoxy, —O—C₆H₄—W, halogen, —O— PO₃H₂, O—PO₂H₂, azido, —NHR₉, —NR₇R₈, —N⁺R₇R₈R₉ Z⁻, in which Z⁻ is the anion of a pharmaceutically acceptable organic or inorganic acid, and R₇, R₈ and R₉ are as defined above or R₇ and R₈ may form, together with the nitrogen atom to which they are bound, a ring of from 3 to 7 members, possibly containing other heteroatoms selected from oxygen, sulphur and nitrogen, possibly substituted with an alkyl, benzyl, or hydroxyethyl radical, in which W is selected from hydrogen, alkyl, alkoxy, nitro, halogen, and hydroxy, and in which the basic and acid groups present in the molecule may possibly be salified with organic or inorganic acids and bases, respectively, to form pharmaceutically acceptable salts;

$R_{13}$ has, independently, the meanings of $R_{12}$, or may be hydrogen;

(4) a group of formula (VII):

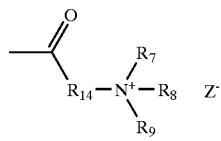
(VII)

in which $R_{14}$ is selected from: a linear or branched alkylene or arylalkylene radical, possibly substituted with a hydroxy group or —O—CO—$R_{15}$, in which $R_{15}$ is an alkyl, alkenyl or arylalkyl radical, $R_7$, $R_8$ and $R_9$ are as defined above, or $R_7$ and $R_8$ may form, together with the nitrogen atom to which they are bound, a ring of from 3 to 7 members as defined above, and $Z^-$ is a pharmaceutically acceptable inorganic or organic anion; and (5) a group of formula (VIII):

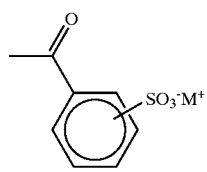
(VII)

in which the —$SO_3^-$ group may be in the ortho, meta or para position relative to the keto group, and $M^+$ is a pharmaceutically acceptable inorganic or organic cation.

2. A compound according to claim 1, wherein $R_2$ and $R_5$ are identical to one another.

3. A compound according to claim 1, wherein $R_3$ and $R_6$ are identical to one another.

4. A compound according to claim 1, wherein $R_1$ is a saturated or mono-unsaturated alkyl radical with from 1 to 23 carbon atoms.

5. A compound according to claim 1, wherein $R_4$ is a saturated or mono-unsaturated alkylene radical with from 1 to 20 carbon atoms.

6. A compound according to claim 1, wherein $R_7$, $R_8$ and $R_9$ are alkyl or alkenyl radicals with from 1 to 7 carbon atoms.

7. A compound according to claim 1, wherein $R_{10}$ is an alkyl radical with from 1 to 20 carbon atoms.

8. A compound according to claim 1, wherein $R_2$ is an alkyl or alkenyl group from 1 to 7 carbon atoms.

9. A compound according to claim 1, wherein Y is an alkylene radical with from 2 to 20 carbon atoms.

10. A compound according to claim 1, wherein X is a cycloalkyl-ether, having a ring with 5 or 6 members.

11. A compound according to claim 1, wherein $R_{11}$ or $R_{12}$ is an alkyl or alkenyl radical with from 1 to 25 carbon atoms.

12. A compound according to claim 1, wherein $R^7$ and $R^8$ form, together with the nitrogen atoms to which they are bound, a ring having from 5 to 7 members.

13. A compound according to claim 1, wherein the —$NR_{12}R_{13}$ group is selected from the group consisting of: piperidinyl, pyrrolidinyl, morpholinyl, piperazinyl and hydroxyethylpiperazinyl groups.

14. A compound according to claim 1, wherein $R_{14}$ is an alkylene radical with from 1 to 10 carbon atoms.

15. A compound according to claim 1, wherein $R_{15}$ is an alkyl or alkenyl radical with from 1 to 7 carbon atoms.

16. A compound according to claim 4, wherein $R_1$ is a saturated or mono-unsaturated alkyl radical with from 13 to 15 carbon atoms.

17. A compound according to claim 5, wherein $R_4$ is a saturated or mono-unsaturated alkylene radical with from 6 to 14 carbon atoms.

18. A compound according to claim 6, wherein $R_7$, $R_8$ and $R_9$ are methyl groups.

19. A compound according to claim 9, wherein Y is an alkylene radical with 2 to 6 carbon atoms.

20. A compound according to claim 10, wherein the members are selected from the group consisting of: tetrahydropyran-2-yl, tetrahydrofuran-2-yl, 4-methoxytetrahydropyran-2-yl, and 1,4-dioxan-2-yl.

21. A compound according to claim 11, wherein $R_{11}$ or $R_{12}$ contains from 1 to 5 heteroatoms selected from the group consisting of: sulphur, oxygen and nitrogen.

22. A compound according to claim 12, wherein the ring contains a further nitrogen atom that is non-substituted or is substituted by a methyl or ethyl group.

23. A compound according to claim 14, wherein $R_{14}$ is an alkylene radical with from 2 to 4 carbon atoms.

24. A pharmaceutical composition comprising the compound according to claim and a pharmaceutically acceptable carrier.

25. A pharmaceutical composition with agonist activity in relation to a CB2 cannabinoid receptor comprising the compound according to claim 24.

26. A cosmetic additive comprising the compound according to claim 1 and a cosmetically acceptable carrier.

27. A method for treating inflammatory processes or inflammatory processes with a hyperalgic component, each process having a neurogenic basis or an immunogenic basis, each basis being associated with a immuno-inflammatory condition, a neurodegenerative pathological condition, or a phathological condition in which an non-psychomimetic effect of cannabinoids mediated either by CB2 receptors or by peripheral CB1 receptors, comprising administering a pharmaceutically effective amount of a compound of claim 1.

* * * * *